(12) United States Patent
Joganic

(10) Patent No.: US 9,592,124 B2
(45) Date of Patent: Mar. 14, 2017

(54) PROTECTIVE EXTERNAL CRANIAL PLATE

(71) Applicant: CRANIAL TECHNOLOGIES, INC., Tempe, AZ (US)

(72) Inventor: Edward Francis Joganic, Phoenix, AZ (US)

(73) Assignee: CRANIAL TECHNOLOGIES, INC., Tempe, AZ (US)

( * ) Notice: Subject to any disclaimer, the term of this patent is extended or adjusted under 35 U.S.C. 154(b) by 20 days.

(21) Appl. No.: 14/588,262

(22) Filed: Dec. 31, 2014

(65) Prior Publication Data

US 2016/0184100 A1    Jun. 30, 2016

(51) Int. Cl.
| A61F 2/50 | (2006.01) |
| A61F 2/28 | (2006.01) |
| A61F 13/12 | (2006.01) |
| A61F 5/058 | (2006.01) |
| A61F 2/78 | (2006.01) |
| A61F 2/30 | (2006.01) |
| A61F 2/46 | (2006.01) |

(52) U.S. Cl.
CPC ............. *A61F 2/2875* (2013.01); *A61F 2/50* (2013.01); *A61F 5/05883* (2013.01); *A61F 5/05891* (2013.01); *A61F 13/12* (2013.01); *A61F 2002/3096* (2013.01); *A61F 2002/30772* (2013.01); *A61F 2002/30957* (2013.01); *A61F 2002/30962* (2013.01); *A61F 2002/4685* (2013.01); *A61F 2002/7806* (2013.01)

(58) Field of Classification Search
CPC .. A61F 2/2875; A61F 2/50; A61F 2002/7806; A61F 2/78; A61F 5/05891; A61F 5/05883; A61F 13/12
See application file for complete search history.

(56) References Cited

U.S. PATENT DOCUMENTS

| 5,218,975 A * | 6/1993 | Prostkoff | ................. A42B 1/08 623/17.19 |
| 2009/0299254 A1* | 12/2009 | Riordan | .................. A61F 13/12 602/53 |
| 2010/0042033 A1* | 2/2010 | Praetzel | ............ A61F 13/00068 128/898 |

* cited by examiner

*Primary Examiner* — David Isabella
*Assistant Examiner* — Suba Ganesan
(74) *Attorney, Agent, or Firm* — Donald J Lenkszus

(57) ABSTRACT

A method and apparatus for preventing brain compression subsequent to removal of a portion of a patient's cranium comprises custom forming a protective external cranial plate. The protective external cranial plate is shaped to approximate the removed portion of the patient's cranium, and to extend peripherally beyond the removed portion. The protective external cranial plate is affixed in airtight and fluid tight engagement to the scalp of the patient.

47 Claims, 6 Drawing Sheets

PROTECTIVE EXTERNAL CRANIAL PLATE

FIELD OF THE INVENTION

The present invention relates to cranial surgery, in general, and to a protective external cranial plate for use subsequent to decompressive craniectomy, in particular.

BACKGROUND

Many conditions, e.g., trauma, tumor, disease, are known to cause the brain to swell, increasing intracranial pressure. In many situations this increase in ICP may be life threatening, requiring a surgical procedure known as a decompressive craniotomy. In this procedure, a large segment of cranial bone, known as the bone flap, is removed from the cranium. The removal of the bone flap relieves the intracranial pressure by allowing the brain to temporarily swell through the hole made in the cranium.

The bone flap is stored, with the intent of returning it to the cranium, once the swelling has subsided and the patient has stabilized, typically 4-6 weeks after the procedure. The bone flap is stored either by surgically inserting it into the abdomen, or by freezing it. By the time the bone flap is to be surgically returned, it often is no longer a viable specimen either due to changing of shape/composition, i.e., remodeling, while in the abdomen or by failing culture tests. In these situations, there are three options available to the surgeon.

One option is fabrication of a custom helmet to protect the affected area. This option is rarely employed.

A second option is the creation of a custom computer generated implant. The implant is attached to the cranium and the scalp is drawn back over the implant Typically the implant fits wonderfully. However, such implants are expensive and require 1 mm fine cut CT scan.

A third option is to use a titanium mesh to cover the hole where the bone has been removed. The mesh is formed from a flat sheet fabricated by the surgeon; or is formed from a prefabricated shape ordered from catalogue. As with the implant, the scalp is drawn back over the mesh.

Both the computer generated implants and titanium mesh solutions are known to have high failure rates. During the 4 to 6 week post-operative period a "dead space" or "void" will occur beneath the region where the bone flap was removed. The mesh may collapse into the void. Even if there is no collapse of the mesh, there is still a void between the brain and the mesh that may become an infection zone.

The cranium may be considered to be like a simple pressure vessel that is held in dynamic equilibrium through arterial (+) and venous (−) pressures and the brain may be considered to be like a sponge. Once the bone flap is removed from the cranium, the brain is exposed to atmospheric pressure that is greater than the intracranial pressure. The atmospheric pressure compresses the brain. The brain is only so elastic, and the rate at which it is compressed can lead to both reversible and irreversible neurological impairment (e.g., loss of speech, mobility upon arising in the morning) and tearing of the nerve fibers.

Accordingly, it is desirable to provide a method and apparatus to protect intracranial contents from the effects of atmospheric pressure.

SUMMARY

In accordance with the principles of the invention, a method and apparatus are provided to protect the intracranial contents from atmospheric pressure.

An embodiment of a method for preventing brain compression subsequent to a portion of a cranium of a patient being removed comprises custom forming a protective external cranial plate for the patient. The custom protective external cranial plate is shaped to approximate the removed portion of the patient's cranium and to extend on the scalp of the patient's head peripherally beyond the removed portion. The portion of the protective external cranial plate extending peripherally beyond the removed portion is shaped to engage the surface of the patient's head. The method further comprises externally affixing the protective external cranial plate to the scalp of the patient.

The method comprises affixing a peripheral edge portion of the protective external cranial plate to the scalp in fluid tight and airtight engagement with the scalp. The method may further comprise using a bio-adhesive to affix the cranial plate to the scalp.

The method further comprises custom forming the protective external cranial plate from a solid material and may comprise custom forming the protective external cranial plate covering from a material that is transparent.

The method may comprise custom forming the protective external cranial plate to have a peripheral portion extending on the scalp outwardly adjacent to the removed portion. The method may comprise custom forming the protective external cranial plate to have the peripheral portion extending continuously around the entire periphery of the removed portion.

The various embodiments of the method may comprise affixing the protective external cranial plate to the scalp in fluid tight and airtight engagement with the scalp around a peripheral edge portion of the protective external cranial plate.

Various embodiments of the method may comprise providing the protective external cranial plate with at least one port. Still further, such embodiments may include providing the at least one port with at least one of a valve, a sensor and a transducer. The at least one port may be utilized to provide negative pressure to allow rehydration of the brain and to enhance affixation to the scalp.

A medical device to prevent brain compression subsequent to removal of a portion of a cranium of a patient comprises a portion shaped to approximate the removed portion of the cranium and an integrally formed peripheral portion extending peripherally outward beyond the removed portion. The peripheral portion is shaped to engage and seal against the scalp of the patient adjacent to the removed portion. The convex portion and the integrally formed peripheral portion form a protective external cranial plate for external application to the scalp of the patient over the removed portion.

The medical device is removably affixable to the scalp with the peripheral edge portion in fluid tight and airtight engagement with the scalp. The peripheral edge portion is removably affixable to the scalp with a bio-adhesive.

The medical device is custom manufactured for the patient. The medical device is custom manufactured from a solid material. The solid material may comprise an optically transparent material.

The medical device peripheral portion extends continuously around the entire periphery of the removed portion.

An embodiment of a medical device comprises a solid convex portion shaped to approximate a removed portion of the cranium of a patient, and a peripheral portion integrally formed with the solid convex portion and extending peripherally outward beyond the removed portion. The peripheral portion is shaped to engage and seal against the scalp of the patient adjacent to the removed portion. The convex portion and the integrally formed peripheral portion form a cranial plate for external application to the scalp of the patient over the removed portion to protect the intracranial contents from atmospheric pressure.

The medical device is custom manufactured for the patient.

A method of manufacturing a protective external cranial plate for external application to the scalp of the patient over a removed portion of the cranium of the patient to protect the intracranial contents of the patient from atmospheric pressure comprises casting a negative impression of the removed portion, forming a positive model from the negative impression, and forming a solid material over the model to produce the cranial plate.

The method may comprise selecting the solid material to comprise a plastic material and may further comprise selecting the material to be transparent.

The method may further comprise trimming the cranial plate to a desired outline and may additionally comprise forming one or more ports in the protective external cranial plate and providing the one or more port with one or more of a valve, a sensor and a transducer.

BRIEF DESCRIPTION OF THE DRAWING

The invention will be better understood from a reading of the following detailed description in conjunction with the drawing figures in which like reference designators are utilized to identify like element, and in which.

DETAILED DESCRIPTION

Figure 1:
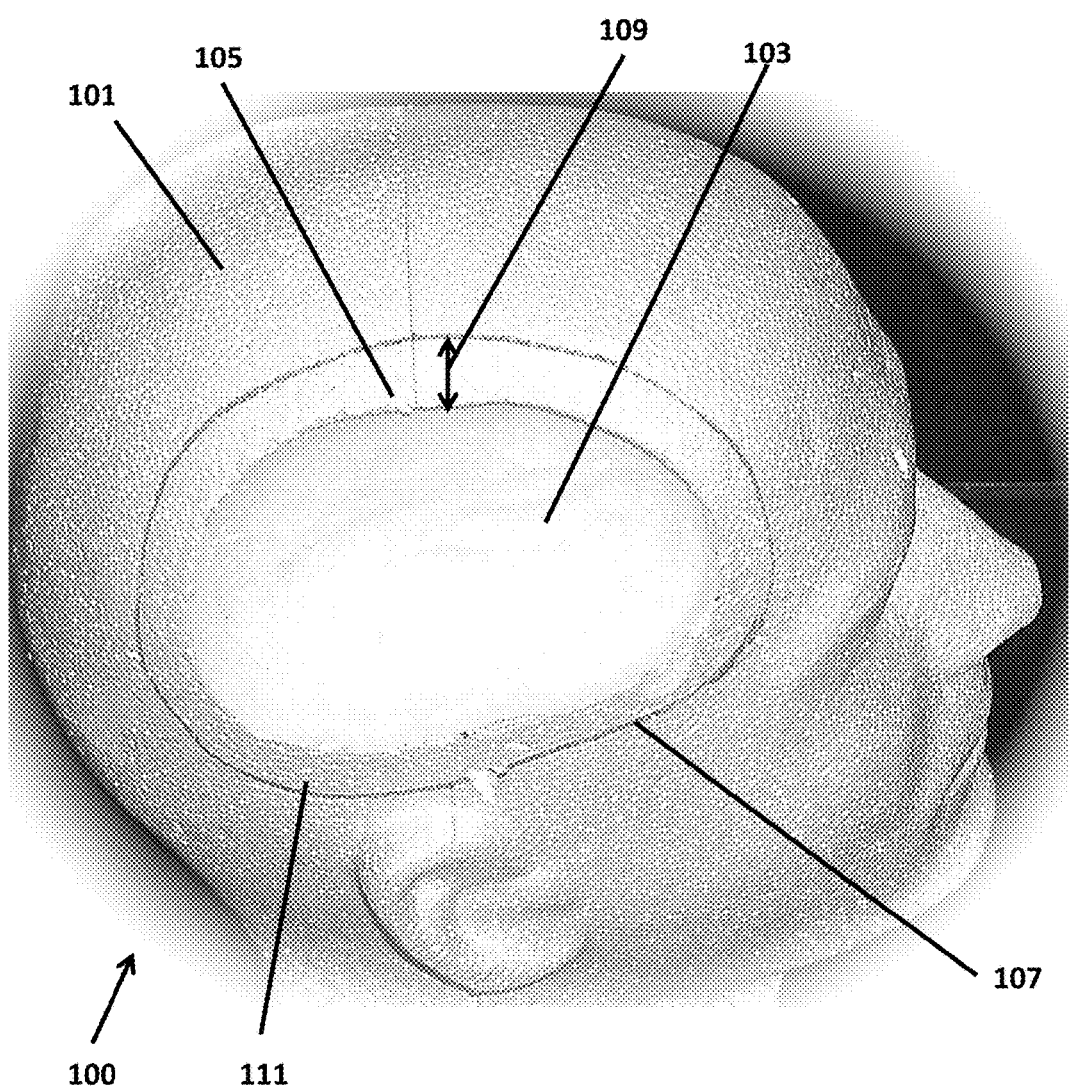
FIG. 1 is a model of a cranium with a removed portion.

Turning now to FIG. 1, a model 100 is shown of a head. Model 100 simulates the head of a patient that has had a decompressive craniotomy. The outer surface 101 of model 100 represents the scalp or skin covering the head. Model 100 includes a concave portion 103 that is representative of the depression that results as a result of a decompressive craniotomy in which a bone flap is removed. Concave portion 103 is bounded by edge 105. Edge 105 is representative of where the scalp covers the edge of the cranial bone. Line 107, which completely encircles concave portion 103, represents the perimeter of a custom manufactured protective external plate 200 shown in FIG. 2. Line 107 is spaced outward from concave portion 103 by a distance 109 forming a circumferential or peripheral scalp portion 111 that surrounds concave portion 103.

Figure 2:
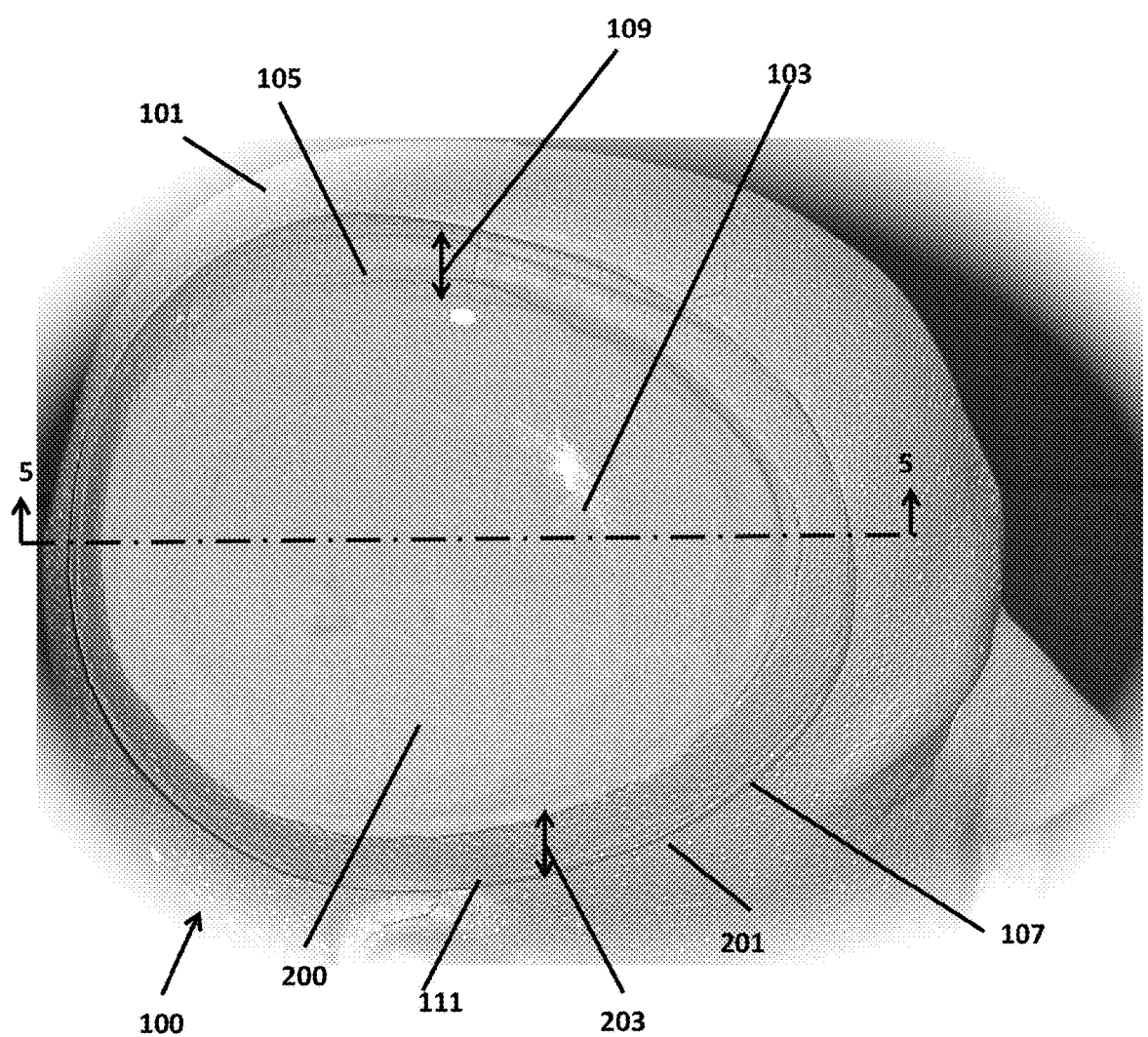
FIG. 2 shows the model of FIG. 1 with a protective external cranial plate.

In FIG. 2, protective external cranial plate 200 is in place on model. Cranial plate 200 is formed from a single sheet of a hard material. In the embodiment shown, cranial plate 200 comprises a polycarbonate material that is optically transparent thereby permitting observation of concave portion 103. Protective external cranial plate 200 fully covers concave portion 103 and extends beyond edge 105 to line 107 along its entire periphery 201 providing a peripheral edge portion 203.

A bio-adhesive is utilized to removably affix peripheral edge portion 203 to the scalp in peripheral scalp portion 111. The bio-adhesive is applied along the entire peripheral edge portion 203. By utilizing a bio-adhesive, protective external cranial plate 200 is sealed in airtight and watertight engagement to peripheral scalp portion 111 covering the bone flap region or concave portion 103. The bio-adhesive utilized is one of a type commonly used with osteotomy products and can be used on skin for years with excellent tolerance.

Figure 3:
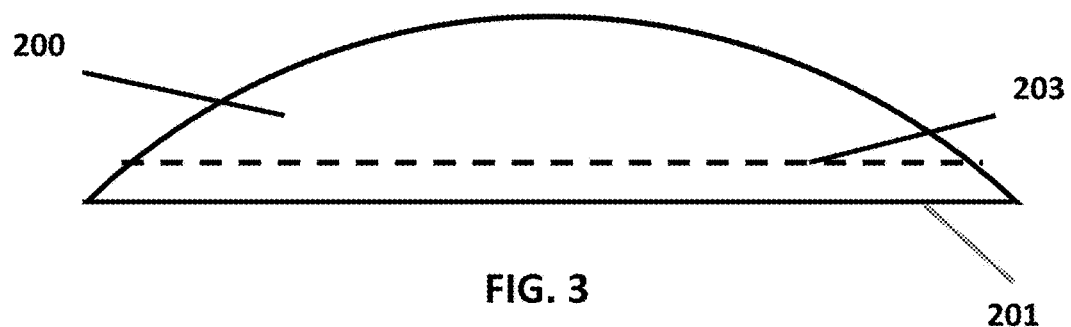
FIG. 3 is a top view of an embodiment of a protective external cranial plate.
Figure 4:
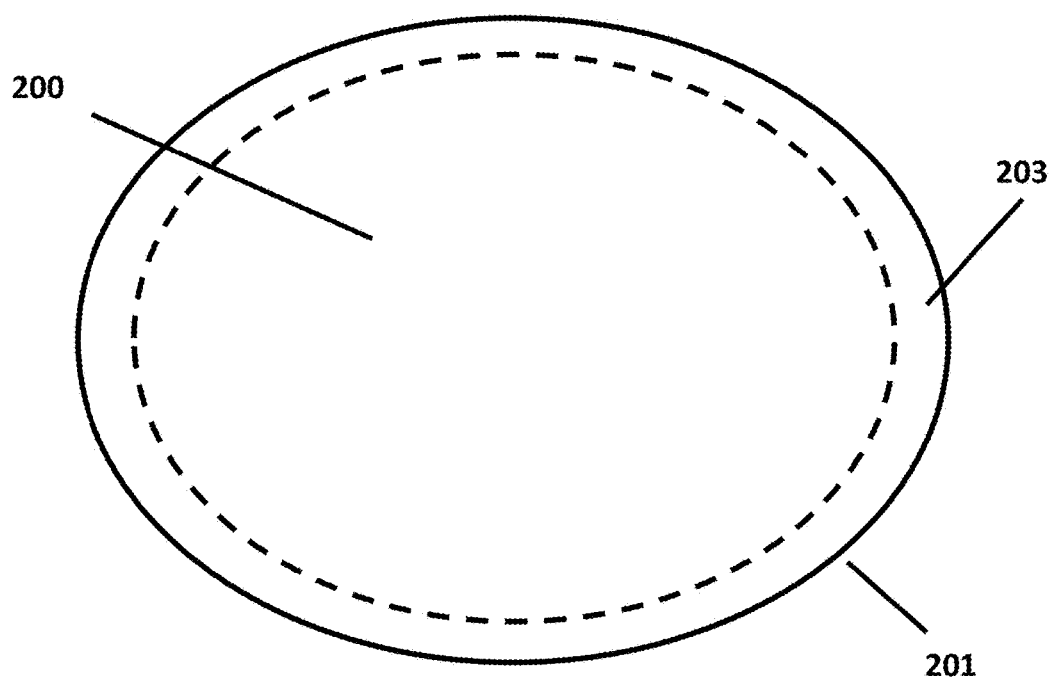
FIG. 4 is a side view of the embodiment of FIG. 3.
Figure 5:
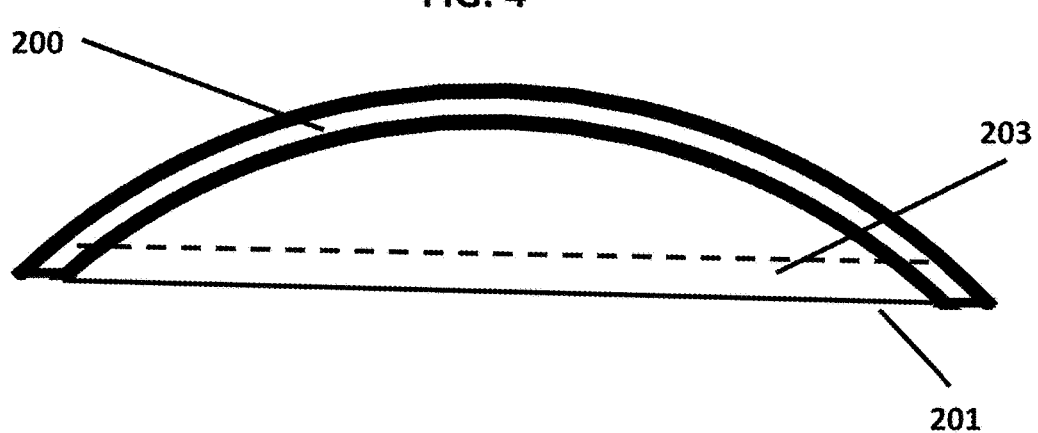
FIG. 5 is a cross-section of the embodiment of FIG. 3 taken along line 5-5.

FIGS. 3, 4 and 5 show an embodiment of protective external cranial plate 200. The side view in FIG. 3 and cross-section view of FIG. 5 clearly show that protective external cranial plate 200 is generally convex and its peripheral edge portion 203 is shaped to mate with the peripheral scalp portion 111.

Figure 6:
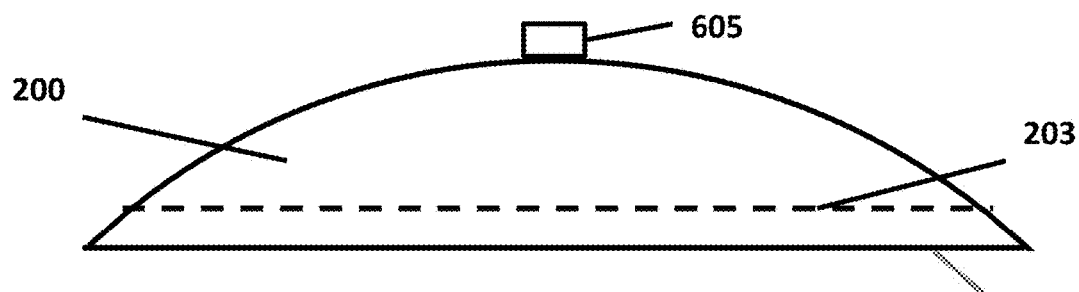
FIG. 6 is a top view of a second embodiment of a protective external cranial plate.
Figure 7:
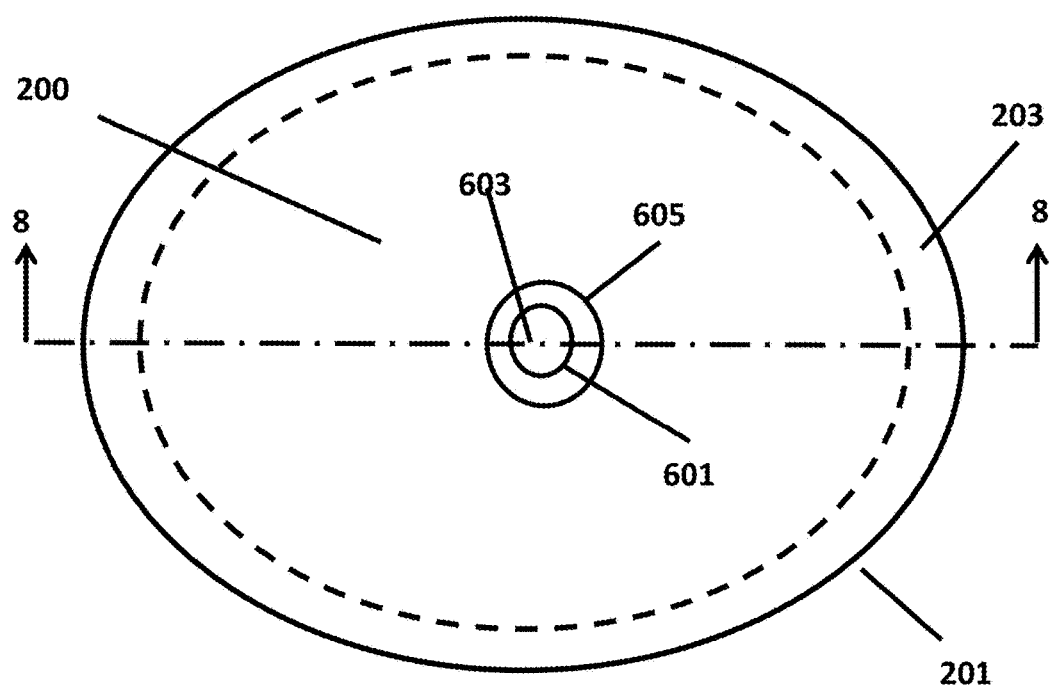
FIG. 7 is a side view of the embodiment of FIG. 6.
Figure 8:
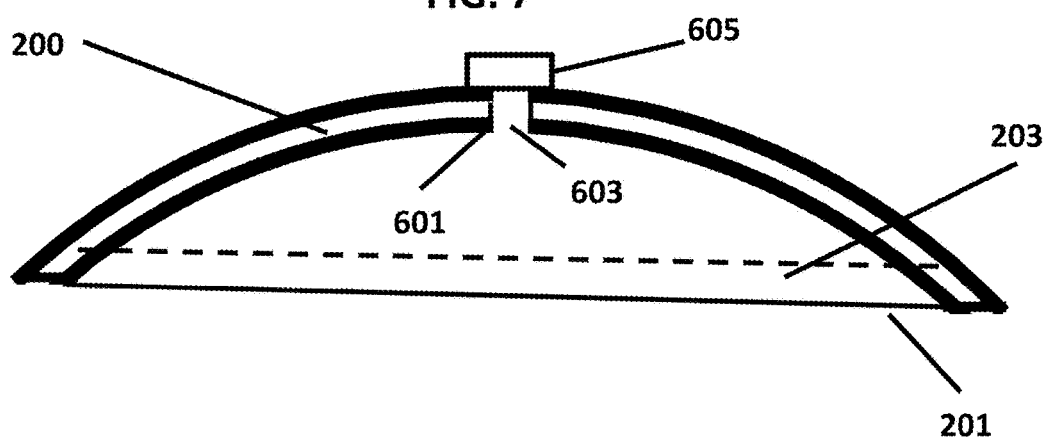
FIG. 8 is a cross-section of the embodiment of FIG. 6 taken along line 8-8 of FIG. 7

Another embodiment of a protective external cranial plate 600 is shown in FIGS. 6, 7, and 8. Protective external cranial plate 600 has at least one port 601 formed therein. Port 601 comprises a through aperture 603. Through aperture 603 may have a valve 605 coupled therein. Valve 605 may be utilized to reduce the pressure under protective external cranial plate 200. Reducing the pressure under protective external cranial plate 200 to less than atmospheric pressure helps adhere external cranial plate 200 to the scalp. In addition reducing the pressure helps prevent cranial collapse and may also allow for rehydration of the brain.

Figure 9:
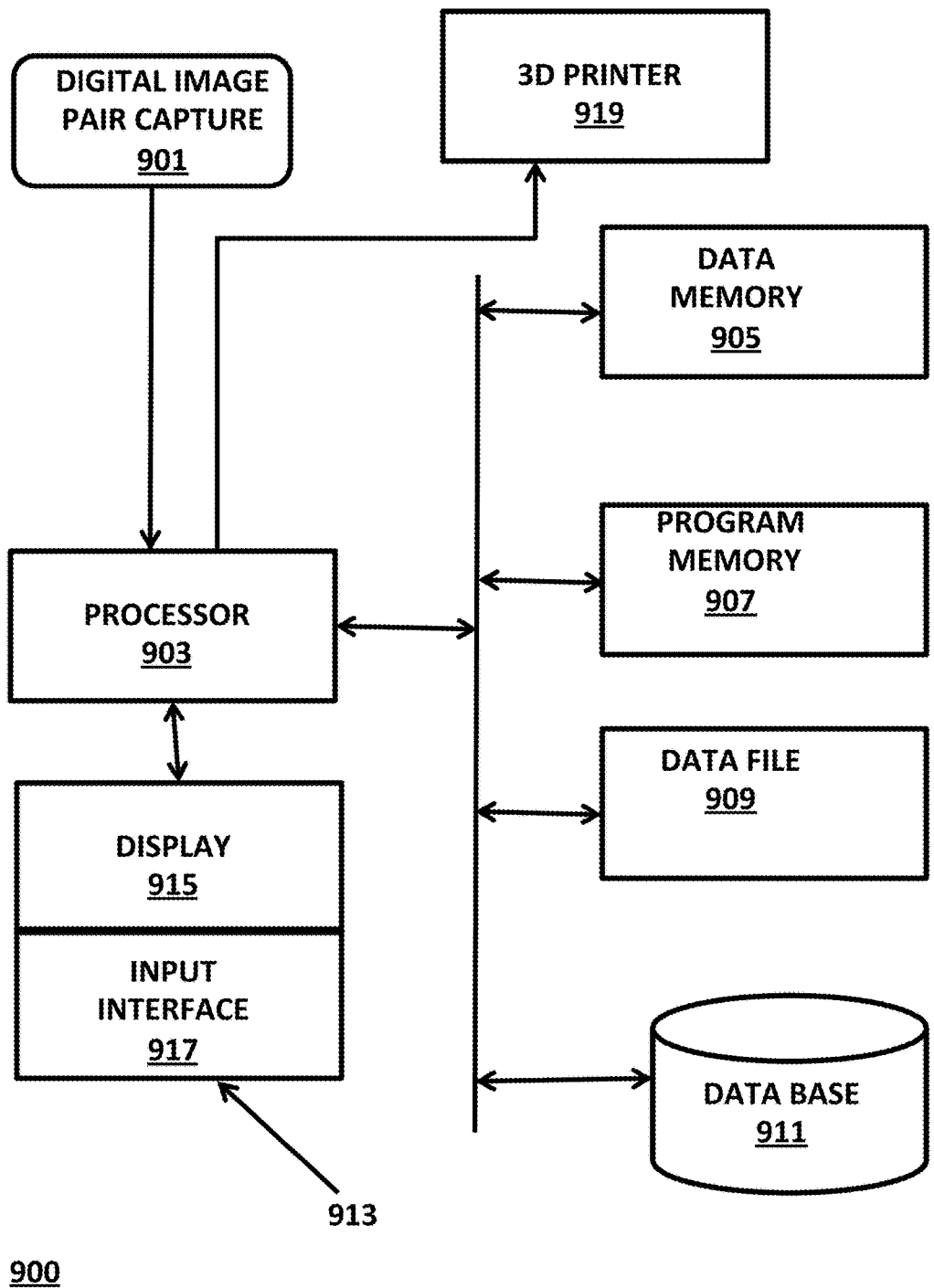
FIG. 9 illustrates steps in a method.

Port 601 may also have a transducer or sensor carried therein. The transducer or sensor may be any transducer or sensor of medical interest such as, e.g., a pressure sensor or humidity sensor. As will be apparent to those skilled in the art FIG. 9 illustrates the method of manufacturing protective external cranial plate 200. At step 901, a negative plaster impression of at least a portion of the cranium including the bone flap region or concave portion 103. At step 903, the negative plaster impression is utilized to form a positive mandrel. The positive mandrel may likewise be formed of plaster. At step 905, a sheet of polycarbonate is heated in an oven to a temperature such that it is shapeable. At step 907, the sheet of polycarbonate is drawn over the positive mandrel. At step 909, the resulting shaped polycarbonate sheet is trimmed to form protective external cranium plate 200. At step 911 an aperture is formed in external cranium plate for receiving one of a valve, transducer or sensor.

Figure 10:
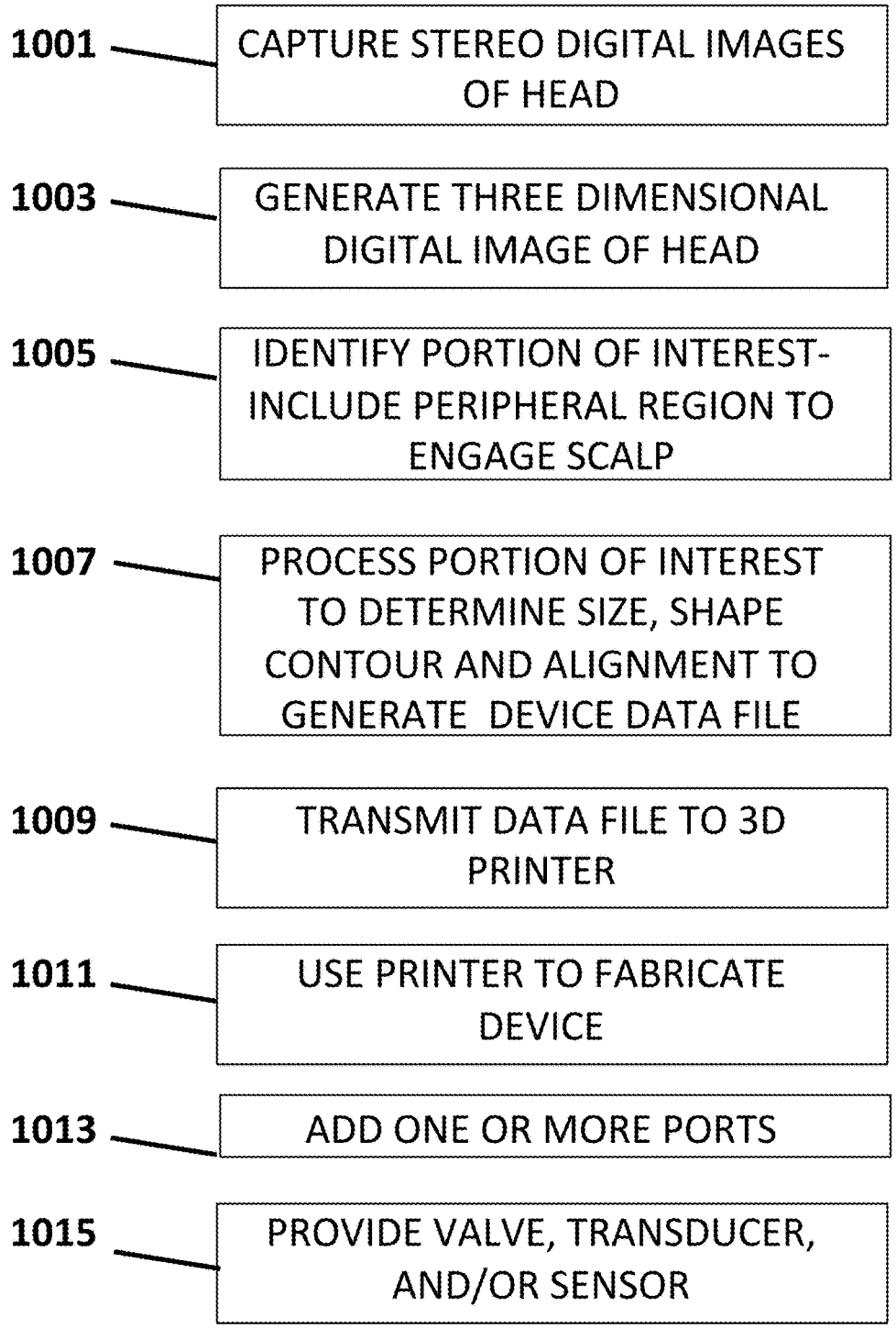
FIG. 10 illustrates steps in a method of forming the embodiment of FIG. 6.

In accordance with an embodiment of a method in accordance with the principles of the invention, shown in FIG. 10, comprises forming a protective external cranial plate for a patient by shaping the protective external cranial plate to approximate a portion of the cranium of the patient at step 1001. The portion comprises an approximation of the cranium that would enclose a removed portion of the cranium of the patient and a portion of the cranium extending on the scalp of the patient around the entire periphery of the removed portion. The portion of the protective external cranial plate extending peripherally beyond the removed portion is shaped to engage the surface of the patient's head. The method further comprises externally affixing the cranial plate to the scalp of the patient at step 1003.

The method comprises affixing a peripheral edge portion of the cranial plate to the scalp in fluid tight and airtight engagement with the scalp at step 1003A. The method may further comprise using a bio-adhesive to affix the cranial plate to the scalp at step 1003B.

The method further comprises custom forming the cranial plate from a solid material at step 1001A and may comprise custom forming the cranial plate covering from a material that is transparent at step 1001B.

The method may comprise custom forming the cranial plate to have a peripheral portion extending on the scalp outwardly adjacent to the removed portion at step 1001C. The method may comprise custom forming the cranial plate to have the peripheral portion extending continuously around the entire periphery of the convex portion 103.

The various embodiments of the method may comprise affixing the cranial plate to the scalp in fluid tight and airtight engagement with the scalp around a peripheral edge portion of the cranial plate at step 1003C.

Various embodiments of the method may comprise providing the protective external cranial plate with a port 601 at step 1005. Still further, such embodiments may include providing port 601 with at least one of a valve, a sensor and a transducer at step 1007. Although only one port is shown in the drawing figures, those skilled in the art appreciate that there may be multiple ports. In other embodiments, the protective external cranial plate may comprise a portion that is transparent rather than it being transparent in its entirety.

It will be further understood by those skilled in the art that various changes and modifications may be made to the method and apparatus of the invention without departing from its spirit or scope. It is intended that the invention not be limited to the embodiments shown and described herein, but that the invention be given the broadest possible scope permissible by law and that the invention is to be limited in scope only by the claims appended hereto.

What is claimed is:

1. A method for preventing brain compression subsequent to removal of a portion of a patient's cranium, said method comprising:
    custom forming a protective external cranial plate, said protective external cranial plate being shaped to approximate said removed portion of said patient's cranium, and to extend peripherally beyond said removed portion;
    shaping said cranial plate to comprise a convex portion shaped to approximate said removed portion of said cranium and an integrally formed peripheral portion contiguous with said convex portion and extending peripherally outward beyond said removed portion, said convex portion and said integrally formed peripheral portion forming a uniformly smooth external surface with a single convex curvature, the entirety of said peripheral portion shaped to engage and seal against said scalp of said patient adjacent to said removed portion;
    configuring said plate to be externally affixed in sealing engagement to said scalp of said patient over said removed portion to protect intracranial contents from the effects of atmospheric pressure; and
    externally affixing said protective external cranial plate to the scalp of said patient to thereby prevent brain compression.

2. A method in accordance with claim 1, comprising:
    affixing said protective external cranial plate to said scalp in fluid tight and airtight engagement with said scalp around said peripheral portion of said protective external cranial plate.

3. A method in accordance with claim 2, comprising:
    using a bio-adhesive to affix said peripheral portion of said protective external cranial plate to said scalp.

4. A method in accordance with claim 1, comprising:
    custom forming said external protective external cranial plate for said patient from a solid material.

5. A method in accordance with claim 1, comprising:
    custom forming at least a portion of said protective external cranial plate from a material that is transparent.

6. A method in accordance with claim 1, comprising:
    custom forming said protective external cranial plate to have said peripheral portion extending continuously around the entire periphery of said removed portion.

7. A method in accordance with claim 1, comprising:
    using a bin-adhesive to affix said protective external cranial plate to said scalp.

8. A method in accordance with claim 7, comprising:
    custom forming said external protective external cranial plate covering for said patient from a solid material.

9. A method in accordance with claim 8, comprising:
    custom forming said external protective external cranial plate covering from a material that is transparent.

10. A method in accordance with claim 1, comprising:
    providing said external protective external cranial plate with at least one port.

11. A method in accordance with claim 10 comprising:
    providing said at least one port with one of a valve and a transducer.

12. A medical device to prevent brain compression subsequent to removal of a portion of a cranium of a patient, said device comprising:
    a convex portion shaped to approximate said removed portion of said cranium; and
    an integrally formed peripheral portion contiguous with said convex portion and extending peripherally outward beyond said removed portion, the entirety of a lower surface of said peripheral portion shaped to engage and seal against the scalp of said patient adjacent to said removed portion;
    said convex portion and said integrally formed peripheral portion forming a uniformly smooth protective external cranial plate with a single convex curvature, said protective external cranial plate configured to be externally affixed in sealing engagement to said scalp of said patient over said removed portion, said protective external plate configured to protect said patient's intracranial contents from the effects of atmospheric pressure to thereby prevent brain compression.

13. A medical device in accordance with claim 12, wherein:
    said medical device is removably affixable to said scalp with said peripheral edge portion in fluid tight and airtight engagement with said scalp.

14. A medical device in accordance with claim 13, comprising:
    said peripheral edge portion is removably affixable to said scalp with a bio-adhesive.

15. A medical device in accordance with claim 12, wherein:
    said medical device is custom manufactured for said patient.

16. A medical device in accordance with claim 15, wherein:
    said medical device is custom manufactured from a solid material.

17. A medical device in accordance with claim 16, wherein:

said solid material comprises an optically transparent material.

18. A medical device in accordance with claim 12, wherein:
said peripheral portion extends continuously around the entire periphery of said removed portion.

19. A medical device in accordance with claim 18, wherein:
said medical device is removably affixable to said scalp with said peripheral edge portion in fluid tight and airtight engagement with said scalp.

20. A medical device in accordance with claim 19, comprising:
said peripheral edge portion is removably affixable to said scalp with a bio-adhesive.

21. A medical device in accordance with claim 20, wherein:
said medical device is custom manufactured for said patient.

22. A medical device in accordance with claim 21, wherein:
said medical device is custom manufactured from a solid material.

23. A medical device in accordance with claim 21, wherein:
said solid material comprises an optically transparent material.

24. A medical device in accordance with claim 12, wherein:
said peripheral edge portion is affixable in fluid tight and airtight engagement with said scalp.

25. A medical device in accordance with claim 12, comprising: at least one port formed therein.

26. A medical device in accordance with claim 25, comprising: one of a valve and a transducer in communication with said at least one port.

27. A medical device comprising:
a solid portion shaped to approximate a removed portion of the cranium of a patient having a convex curvature; and
a peripheral portion contiguous with said solid portion and integrally formed with said solid portion and extending peripherally outward beyond said removed portion, the entirety of said peripheral portion shaped to engage and seal against the scalp of said patient adjacent to said removed portion;
said solid portion and said integrally formed peripheral portion forming a protective external cranial plate configured to be externally affixed in sealing engagement to the scalp of said patient over said removed portion, said protective external plate configured to protect intracranial contents of said cranium from atmospheric pressure to prevent cranial compression, said solid portion and said integrally formed peripheral portion providing a single smooth upper surface with a single convex curvature.

28. A medical device in accordance with claim 27, wherein:
said medical device is removably affixable to said scalp with said peripheral edge portion in fluid tight and airtight engagement with said scalp.

29. A medical device in accordance with claim 28, comprising:
said peripheral edge portion is removably affixable to said scalp with a bio-adhesive.

30. A medical device in accordance with claim 27, wherein:
said medical device is custom manufactured for said patient.

31. A medical device in accordance with claim 30, wherein:
said medical device is custom manufactured from a solid material.

32. A medical device in accordance with claim 31, wherein:
said solid material comprises an optically transparent material.

33. A medical device in accordance with claim 27, wherein:
said peripheral portion extends continuously around the entire periphery of said removed portion.

34. A medical device in accordance with claim 33, wherein:
said medical device is removably affixable to said scalp with said peripheral edge portion in fluid tight and airtight engagement with said scalp.

35. A medical device in accordance with claim 34, comprising:
said peripheral edge portion is removably affixable to said scalp with a bio-adhesive.

36. A medical device in accordance with claim 35, wherein:
said medical device is custom manufactured for said patient.

37. A medical device in accordance with claim 36, wherein:
said medical device is custom manufactured from a solid material.

38. A medical device in accordance with claim 37, wherein:
said solid material comprises an optically transparent material.

39. A medical device in accordance with claim 27, wherein:
said peripheral edge portion is affixable in fluid tight and airtight engagement with said scalp.

40. A medical device in accordance with claim 27, comprising: at least one port formed on said solid portion.

41. A medical device in accordance with claim 40, comprising: one of a valve and a transducer in communication with said at least one port.

42. A method of manufacturing a protective external cranial plate for external application to the scalp of said patient over a removed portion of the cranium of said patient to protect the intracranial contents of said patient from atmospheric pressure, comprising:
casting a negative impression of said removed portion;
forming a positive mandrel from said negative impression;
forming a solid material over said mandrel to produce said protective external cranial plate
shaping said protective external cranial plate to comprise a convex portion shaped to approximate said removed portion of said cranium and an integrally formed peripheral portion contiguous with said convex portion, said peripheral portion extending peripherally outward beyond said removed portion, said peripheral portion shaped to engage and seal against said scalp of said patient adjacent to said removed portion said integrally formed peripheral portion and said convex portion providing a uniformly smooth outer surface with a single convex curvature; and
configuring said plate to be externally affixed in sealing engagement to said scalp of said patient over said removed portion to protect intracranial contents from the effects of atmospheric pressure to prevent cranial compression.

43. A method in accordance with claim 42, comprising: selecting said solid material to comprise a plastic material.

44. A method in accordance with claim 43, comprising: selecting said material to be transparent.

45. A method in accordance with claim 42, comprising: trimming said protective external cranial plate to a desired outline.

46. A method in accordance with claim 42, comprising: forming at least one port in said protective external cranial plate.

47. A method in accordance with claim 42, comprising: providing said at least one port with one of a valve and a transducer.

* * * * *